(12) United States Patent
Khanuja et al.

(10) Patent No.: US 7,135,590 B2
(45) Date of Patent: Nov. 14, 2006

(54) GALLIC ACID DERIVATIVE AND PROCESS OF PREPARING THE SAME

(75) Inventors: Suman Preet Singh Khanuja, Uttar Pradesh (IN); Mahendra Pandurang Darokar, Uttar Pradesh (IN); Ankur Garg, Uttar Pradesh (IN); Togarrati Padmapriya, Uttar Pradesh (IN); Ajit Kumar Shasany, Uttar Pradesh (IN); Arvind Singh Negi, Uttar Pradesh (IN); Sunia Kumar Chattopadhyay, Uttar Pradesh (IN); Kachin Srivastava, Uttar Pradesh (IN); Asish Kumar Bhattacharya, Uttar Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/919,567

(22) Filed: Aug. 17, 2004

(65) Prior Publication Data

US 2005/0181950 A1 Aug. 18, 2005

Related U.S. Application Data

(63) Continuation of application No. PCT/IN03/00436, filed on Dec. 31, 2003.

(51) Int. Cl.
C07C 69/76 (2006.01)
C07C 39/14 (2006.01)
(52) U.S. Cl. ..................... 560/100; 568/735
(58) Field of Classification Search ........... 560/8, 560/55, 100, 205, 101, 102, 59, 61, 63, 51, 560/52, 53; 71/27
See application file for complete search history.

(56) References Cited

OTHER PUBLICATIONS

Negri et al., Bioorganic & Medicinal Chemistry Letters (2005), 15(4), 1243-1247.*

* cited by examiner

Primary Examiner—Thurman K. Page
Assistant Examiner—Karl Puttlitz
(74) Attorney, Agent, or Firm—Renner, Otto, Boisselle & Sklar, LLP

(57) ABSTRACT

This invention provides a plant growth regulatory activity of a new biologically active synthetic molecule methanone-(3', 4',5'-trimethoxy) phenyl, 1-naphthyl, 2-O-4"-ethyl but-2"-enoate. More particularly, the invention relates to the potent plant growth promoting activity of a gallic acid derivative having a structure represented by Formula 1 and a molecular formulae $C_{26}H_{26}O_7$. This invention also provides a novel process for preparation of said molecule from a naturally occurring compound and testing it for growth regulating activity using Bacopa test system developed at CIMAP (Khanuja et al., 2001)

Formula 1

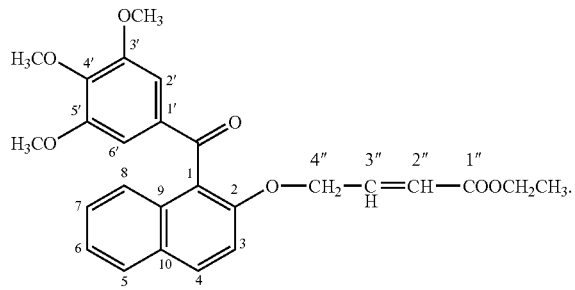

55 Claims, No Drawings

GALLIC ACID DERIVATIVE AND PROCESS OF PREPARING THE SAME

RELATED APPLICATIONS

This application is a continuation of PCT Application No. PCT/IN03/00436, filed Dec. 31, 2003, which designates the United States. PCT Application No. PCT/IN03/00436 is hereby incorporated by reference in its entirety.

FIELD OF THE INVENTION

This invention provides a plant growth regulatory activity of a new biologically active synthetic molecule methanone-(3',4',5'-trimethoxy) phenyl, 1-naphthyl 2-O-4"-ethyl but-2"-enoate. More particularly, the invention relates to the potent plant growth promoting activity of a gallic acid derivative having the structural Formula 1 (also referred to as Compound 1) and molecular formula $C_{26}H_{26}O_7$. This invention also provides a novel process for preparation of a molecule from a naturally occurring compound and testing it for growth regulating activity using Bacopa test system developed at CIMAP (Khanuja et al 2001).

Formula 1

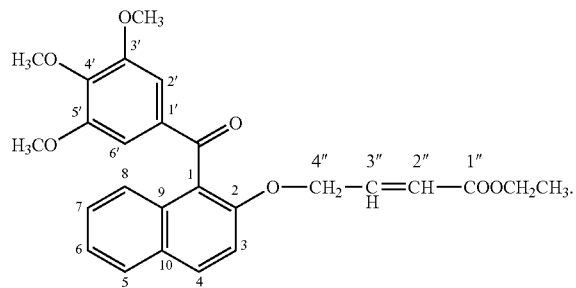

BACKGROUND OF THE INVENTION

Plant growth substances occupy an important place in the growth and developmental processes of all plant species. The pioneers in plant growth substances, Charles Darwin, Boycen-Jensen, and others, recognized that plant growth phenomenon was under control of some chemical substances produced by the plants and in 1928 F. W. Went successfully demonstrated the existence of growth-regulating substances in plants. These compounds are useful for altering a plant's life processes or structure in some beneficial way so as to enhance yield, improve quality or facilitate harvesting. The plant growth hormones, auxins from oat seedlings, and gibberellins from a fungus, and several secondary plant products such as phenolics, lipids, steroids and terpenoids were shown to be responsible for plant growth and development. One class of plant hormone, auxins, and their synthetic mimics are of particular interest. Auxin-like activity is known to affect a number of plant processes, such as cell division, rooting at the basal end of shoots, shoot elongation, apical dominance, phototropic responses and control of abscission of organs such as buds, flowers, fruits, leaves and the like. Some of the latter elicit growth responses in conjunction with the endogenous growth hormones. Certain synthetic compounds, although different than the natural growth substances, also induce similar biological responses. Synthetic polyhydroxylated steroidal lactones are found to be highly effective plant growth promoting substances (Thompson et al., *J. Org. Chem.*, 44, pp. 5002 to 5004, 1979; Thompson et al.—U.S. Pat. No. 4,346,226). Several oligosaccharins, brassinolides and jasmonates have been reported as non-traditional regulators of plant growth, development and gene expression (Clouse S. D. (1996), *Plant J.*, 10, pp. 1 to 8).

Plant-growth regulators with auxin-like activity comprise an important class of chemicals for use in agriculture. As of 1994, there were approximately 29 compounds with auxin-like activity approved for agricultural use worldwide. Of these compounds, 21 were approved for use in the United States (*Kirk-Othmer Encyclopedia of Chemical Technology*, 4th Ed., Kroschwitz et al., Eds., John Wiley & Sons, New York, 1994). A particularly widely used synthetic auxin is 2,4-dichlorophenoxyacetic acid (2,4-D). Among its many uses, 2,4-D is sprayed on the foliage of citrus trees in California and Florida (also in citrus growing countries such as Israel, Spain, Morocco, South Africa, etc.) to prevent pre-harvest fruit drop and to increase fruit size.

The agricultural application of exogenous chemicals to food crops is coming under increased scrutiny by many segments of society including the agricultural industry, advocates for agricultural laborers, environmental groups and consumers. In the United States, agricultural industry concerns stem from the fact that plant growth regulators must be officially registered with the Environmental Protection Agency (EPA) before they can be used or sold. Additionally, as plant-growth regulators are often applied closer to harvest than are pesticides, the actual practical requirements for their safety are more stringent.

The screening process associated with the official registration is both time-consuming and expensive. This process includes evaluation of a plant-growth regulator's safety hazards to humans, the environment and non-target species. Further, acute and chronic toxicity must be determined. The agricultural industry shoulders a portion of the costs of the pre-registration program in higher prices. Further, the industry typically bears part of the financial burden for re-registering the compound for a particular use. For example, the California citrus industry paid approximately two million dollars to effect the re-registration of 2,4-D as a pre-harvest fruit drop inhibitor. In addition to these financial concerns, the potential toxicity of synthetic plant-growth regulators raises additional concerns regarding the safety of their use.

The concerns of environmental groups, advocates for agricultural laborers and consumers arise from the potential toxicity of plant-growth regulators. For example, auxin mimics such as 2,4-D and related phenoxy acids have moderately acute toxicity and are moderate in their local effects upon the skin or eyes. Results of cytogenic studies in Sweden indicate that, in practice, 2,4-D constitutes a cytogenic hazard to man. Additionally, 2,4-D has been found to exhibit central nervous system toxicity.

In light of their utility in preventing pre-harvest fruit drop and increasing fruit size, coupled with the expense of registration, re-registration and the potential toxicity of auxin mimics, alternatives to the use of synthetic auxins are being actively sought.

The application to plants and soils of natural auxins and natural auxin precursors is a particularly promising alternative to the use of synthetic auxin mimics. For instance, L-tryptophan has been reported to serve as precursor for the microbial formation of indole-3-acetic acid (IAA) (e.g., Arshad and Frankenberger, *Plant Soil*, 133, pp. 1 to 8 (1991)). Further, the synthesis of IAA upon application of tryptophan to soil has been shown to promote plant growth. For instance, growth of Douglas fir was increased by application of tryptophan and inoculation with a fungus capable of producing IAA from tryptophan. When tryptophan was applied to soils under aseptic conditions (i.e., steam-sterilized soil), L-TRP conversion to IAA was not observed (Martens and Frankenberger, *Soil Science*, 155, pp. 263 to 271 (1993)). Thus, it was concluded that the conversion of tryptophan to IAA was a microbe-mediated process. Certain synthetic compounds, although different than the natural growth substances, also induce similar biological responses. Synthetic polyhydroxylated steroidal lactones are found to be highly effective plant growth promoting substances. Several oligosaccharins, brassinolides and jasmonates have been reported as non-traditional regulators of plant growth, development and gene expression. An efficient and novel plant system as biosensor for detecting the environmental hazards and bioactive molecules through distinct responses has been developed at CIMAP and is being used for testing new molecules for their biological activities including plant growth regulators.

SUMMARY OF THE INVENTION

This invention provides a novel biologically active synthetic compound, methanone-(3',4',5'-trimethoxy)phenyl, 1-naphthyl, 2-O-4"-ethyl but-2"-enoate. More particularly, the invention relates to the development of a new synthetic molecule with potent plant growth regulator activity having the structural Formula 1 (as shown above). This invention also provides a process for preparation of the molecule from a naturally occurring compound. The molecule in question is a light yellow oil, having molecular formula $C_{26}H_{26}O_7$. Further the invention provides plant growth promoting activity of a gallic acid derivative using a plant biosensor system "Bacopa test". This invention also provides efficient and economical process for the production of the molecule.

OBJECTS OF THE INVENTION

One object of the present invention is to provides a novel gallic acid derivative, methanone-(3',4',5'-trimethoxy) phenyl, 1-naphthyl, 2-O-4"-ethyl but-2"-enoate, $C_{26}H_{26}O_7$ having structural Formula 1.

Another object of the present invention is to provide a novel gallic acid derivative, methanone-(3',4',5'-trimethoxy) phenyl, 1-naphthyl, 2-O-4"-ethyl but-2"-enoate, $C_{26}H_{26}O_7$, represented by structural Formula 1, useful as a plant growth regulator.

Another object of the present invention relates to a novel gallic acid derivative, 2-O-naphthyl, 3',4',5'-trimethoxy benzoate, having structural Formula 4 and molecular formula $C_{20}H_{18}O_5$, and its usefulness as plant growth regulator in development of plants.

Yet another object of the present invention is to provide a novel gallic acid derivative methanone-(3',4',5'-trimethoxy) phenyl, 1-naphthyl, 2-ol, having structural Formula 5 (also referred to as Compound 5) and molecular formula $C_{17}H_{18}O_5$, capable of plant growth regulation compound, obtained during synthesis of compound represented by Formula 1.

Still another object of the present invention provides an efficient and economical process for the preparation of this biologically active compound represented by structural Formula 1 with higher yields from a readily available starting material.

To the accomplishment of the foregoing and related ends, the invention, then, comprises the features hereinafter fully described and particularly pointed out in the claims. These embodiments are indicative, however, of but a few of the various ways in which the principles of the invention may be employed. Other objects, advantages and features of the invention will become apparent from the following detailed description of the invention.

DETAILED DESCRIPTION

Accordingly, one embodiment of the present invention relates to a novel synthetic plant growth regulator compound, methanone-(3',4',5'-trimethoxy) phenyl, 1-naphthyl, 2-O-4"-ethyl but-2"-enoate having structural Formula 1 and having molecular formula $C_{26}H_{26}O_7$,

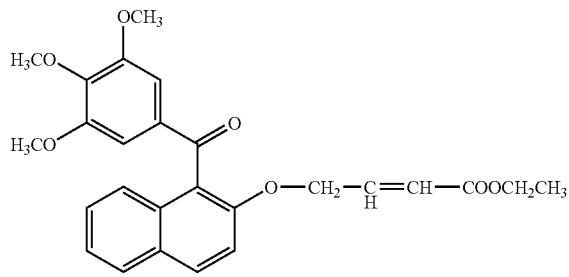

Formula 1

Another embodiment of the present invention relates to a novel compound, methanone-(3',4',5'-trimethoxy) phenyl, 1-naphthyl, 2-ol, having structural Formula 5 and molecular formula $C_{17}H_{18}O_5$, capable of plant growth regulation, obtained during synthesis of the compound represented by Formula 1,

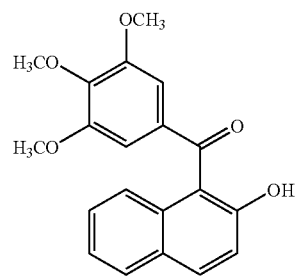

Formula 5

Still another embodiment of the present invention relates to a compound represented by Formula 1, wherein the compound having Formula 1 has auxin like plant growth regulatory activity.

Yet another embodiment of the present invention relates to a compound represented by Formula 1, wherein the compound enhances the shoot elongation by about 2 cm within 15 days.

Another embodiment of the present invention relates to a compound represented by Formula 1, wherein the compound enhances the shoot elongation by about 1.6 cm within 15 days.

One more embodiment of the present invention relates to a compound represented by Formula 1, wherein the compound produces about 2 to 5 shoots within three weeks in medium A3.

Still another embodiment of the present invention relates to a compound represented by Formula 1, wherein the compound produces about 3 to 4 shoots within three weeks in medium A3.

Another embodiment of the present invention relates to a compound of Formula 1, wherein the compound is more effective at low concentrations in enhancing the callus formation and shoot differentiation.

Yet another embodiment of the present invention relates to a process for preparing a compound represented by structural Formula 1, i.e. methanone-(3',4',5'-trimethoxy) phenyl, 1-naphthyl, 2-O-4"-ethyl but-2"-enoate and having a molecular formulae $C_{26}H_{26}O_7$, the process comprising the steps of:

(a) methylating gallic acid by treating it with a methylating agent and an alkali compound in a suitable solvent reaction medium to obtain intermediate having a structural Formula 3, i.e 3,4,5-trimethoxy benzoic acid;

(b) reacting the 3,4,5-trimethoxy benzoic acid obtained in step (a) with 2-naphthol in the presence of a carboxylic acid activator in the presence of a suitable base and an organic solvent to obtain an intermediate compound having a structure as represented by Formula 4 and molecular formula $C_{20}H_{18}O_5$;

(c) purifying the compound having structural Formula 4 obtained in the step (b) by column chromatography;

(d) subjecting the compound having structural Formula 4 of step (c) to Fries rearrangement in presence of appropriate Lewis acid at a temperature in the range of about 50 to about 150° C., followed by purification by column chromatography to yield an intermediate having a structure represented by Formula 5, a molecular formula $C_{17}H_{18}O_5$, and a yield in the range of about 15 to about 40%; and (e) reacting the intermediate having structural Formula 5 from step (d) with an alkyl halo-crotonate in a suitable reaction medium consisting of a base and a suitable organic solvent to yield methanone-(3',4',5'-trimethoxy) phenyl, 1-naphthyl, 2-O-4"-ethyl but-2"-enoate, having a structure represented by Formula 1, a molecular formula $C_{26}H_{26}O_7$, with a yield in the range of about 45 to about 75%.

Still another embodiment of the present invention relates to a methylating agent utilized in step (a), wherein the methylating agent is selected from the group comprising of dimethyl sulphate or methyl iodide.

Yet another embodiment of the present invention relates to a methylating agent, wherein methylating agent used is dimethyl sulphate.

One more embodiment of the present invention relates to the amount of methylating agent utilized in step (a), wherein the amount of methylating agent used is in the range of about 20 to about 30 ml.

One more embodiment of the present invention relates to the amount of methylating agent utilized in step (a), wherein the amount of methylating agent used is in the range of about 21 to about 28 ml.

Yet another embodiment of the present invention relates to the alkali compound utilized in step (a), wherein the alkali compound is selected from sodium hydroxide, potassium hydroxide or lithium hydroxide.

Another embodiment of the present invention relates to the alkali compound utilized in step (a), wherein alkali used is sodium hydroxide or potassium hydroxide.

Still another embodiment of the present invention relates to the amount of alkali compound utilized in step (a), wherein the amount of alkali compound used is in the range of about 10 to about 25 g.

Still another embodiment of the present invention relates to the amount of alkali compound utilized in step (a), wherein the amount of alkali compound used is in the range of about 16 to about 20 g.

One more embodiment of the present invention relates to the solvent utilized in step (a), wherein the solvent is selected from water, methanol and acetone.

Yet another embodiment of the present invention relates to the solvent utilized in step (a), wherein solvent used in step (a) is water.

Another embodiment of the present invention relates to the amount of solvent utilized in step (a), wherein the amount of solvent used is in the range of about 50 to about 120 ml.

Another embodiment of the present invention relates to the amount of solvent utilized in step (a), wherein the amount of solvent is in the range of about 60 about 100 ml.

Still another embodiment of the present invention relates to the amount of 2-naphthol utilized in step (b), wherein the amount of 2-naphthol utilized is in the range of about 2 to 5 g.

Still another embodiment of the present invention relates to the amount of 2-naphthol utilized in step (b), wherein the amount of 2-naphthol utilized is in the range of about 3.6 to about 4 g.

Yet another embodiment of the present invention relates to the activator utilized in step (b), wherein the activator is selected from dicyclohexyl carbodiimide (DCC) and N-(3-dimethylaminopropyl)-N'-ethyl carbodiimide hydrochloride (EDC).

Still another embodiment of the present invention relates to the activator utilized in step (b), wherein the activator used is DCC.

One more embodiment of the present invention relates to the amount of activator utilized in step (b), wherein the amount of activator used is in the range of about 2 to about 5 g.

One more embodiment of the present invention relates to the amount of activator utilized in step (b), wherein the amount of activator is in the range of about 3.6 to about 4 g.

Another embodiment of the present invention relates to base utilized in step (b), wherein the base is selected from dimethyl amino pyridine (DMAP) or triethyl amine (TEA).

Yet another embodiment of the present invention relates to the amount of base utilized in step (b), wherein the amount of base used is in the range of about 25 to about 60 g.

Yet another embodiment of the present invention relates to the amount of base utilized in step (b), wherein the amount of base is in the range of about 30 to about 50 g.

Still another embodiment of the present invention relates to organic solvent utilized in step (b), wherein the organic solvent is selected from dichloromethane or dimethyl formamide.

One more embodiment of the present invention relates to organic solvent utilized in step (b), wherein organic solvent is dichloromethane.

Another embodiment of the present invention relates to the amount of organic solvent utilized in step (b), wherein the amount of organic solvent used is in the range of about 30 to about 80 ml.

Another embodiment of the present invention relates to the amount of organic solvent utilized in step (b), wherein the amount of organic solvent used is in the range of about 40 to about 70 ml.

Still another embodiment of the present invention relates to the column chromatography utilized in steps (c) and (d), wherein in the column chromatography of steps (c) and (d) the adsorbent utilized therein is selected from silica gel, silicic acid or fluorosil.

One more embodiment of the present invention relates the adsorbent utilized in the column chromatography of steps (c) and (d), wherein the adsorbent used is silica gel.

Another embodiment of the present invention relates to the temperature at which step (d) is conducted, wherein the temperature is in the range of about 60 to about 130° C.

Yet another embodiment of the present invention relates Lewis acid utilized in step (d), wherein the Lewis acid is selected from aluminum chloride, zinc chloride or polyphosphoric acid.

Another embodiment of the present invention relates to the Lewis acid utilized, wherein the Lewis acid used is aluminum chloride.

One more embodiment of the present invention relates to the amount of Lewis acid utilized in step (d), wherein the amount of Lewis acid used is in the range of about 1 to about 5 g.

One more embodiment of the present invention relates to the amount of Lewis acid utilized in step (d), wherein the amount of Lewis acid used is in the range of about 2 to about 3 g.

Still another embodiment of the present invention relates to the yield of methanone-(3',4',5'-trimethoxy) phenyl, 1-naphthyl, 2-ol intermediate having a structural Formula 5 and molecular formula $C_{17}H_{18}O_5$ obtained in step (d), wherein the yield obtained in step (d) of the compound is in the range of about 20 to about 31.2%.

One more embodiment of the present invention relates to the alkyl halo crotonate utilized in step (e), wherein the alkyl halo crotonate is selected from methyl chloro crotonate, methyl bromo crotonate or ethyl bromo crotonate.

Still another embodiment of the present invention relates to the alkyl halo crotonate utilized in step (e), wherein alkyl halo crotonate is ethyl bromo crotonate.

Another embodiment of the present invention relates to the amount of alkyl halo crotonate utilized in step (e), wherein the amount of alkyl halo crotonate used is in the range of about 0.1 to about 1.5 ml.

Another embodiment of the present invention relates to the amount of alkyl halo crotonate utilized in step (e), wherein the amount of alkyl halo crotonate used is in the range of about 0.2 to about 0.5 ml.

One more embodiment of the present invention relates to the base utilized in step (e), wherein the base is selected from potassium hydroxide, sodium hydroxide or potassium carbonate.

Still another embodiment of the present invention relates to the base utilized in step (e), wherein the base used is potassium carbonate.

Yet another embodiment of the present invention relates to the amount of base utilized in step (e), wherein the amount of base used in the range of about 0.5 to about 3 g.

Yet another embodiment of the present invention relates to the amount of base utilized in step (e), wherein the amount of base used is in the range of about 1 to about 2 g.

Another embodiment of the present invention relates to the organic solvent utilized in step (e), wherein the organic solvent is selected from dimethyl formamide, acetone or methanol.

One more embodiment of the present invention relates to the organic solvent utilized in step (e), wherein the organic solvent used is acetone.

Still another embodiment of the present invention relates to the amount of organic solvent utilized in step (e), wherein the amount of organic solvent used is in the range of about 5 to about 15 ml.

Still another embodiment of the present invention relates to the amount of organic solvent utilized in step (e), wherein the amount of organic solvent used is in the range of about 6 to about 10 ml.

One more embodiment of the present invention relates to the yield obtained of methanone-(3',4',5'-trimethoxy) phenyl, 1-naphthyl, 2-O-4"-ethyl but-2"-enoate, having structural Formula 1 and molecular formula $C_{26}H_{26}O_7$, in step (e), wherein the yield of the compound is in the range of about 47 to about 70%.

The invention is described in detail in the examples given below which are provided to illustrate the invention and therefore should not be construed to limit the scope of the invention.

EXAMPLES

Example 1

Growth Promoting Activity of Compound 1 Using Bacopa Sensor System

For testing the growth promoting effect of methanone-(3',4',5'-trimethoxy) phenyl, 1-naphthyl, 2-O-4"-ethyl but-2"-enoate, the compounds was dissolved in DMSO and added into the medium at 1.0 µg/ml. Only solvent was used as a control in the experiment for comparison. A fast propagating strain of *Bacopa monnieri* developed as a biosensor system through tissue culture at CIMAP (Khanuja et al., 2001, *J Environa Pathol, Toxicol and Onco* (JEPTO), 20:pp. 15 to 22) was used in the tests. The MS basal medium (Murashige and Skoog, 1962, *Physiol. Planta.* 15: pp. 473 to 497) supplemented with test compounds was used in the assays. Measured 0.5 to 1.0 ml medium was poured into 1.5 ml graduated microcentrifuge tubes. Twig cuttings of 2.5 cm were inoculated in 10 replicates for each treatment. These inoculated tubes were put into a half transparent desiccator allowing air passage through sterile cotton plugs fixed on opening vent. The tubes were placed such that the medium-containing portion of the tubes where roots would be initiating is inserted in to the holes of the stand made from a thermocol sheet. These desiccators were incubated at normal ambient temperature of 25 to 28° C. with 14 hours light and 10 hours dark cycle. The root initiation, shoot elongation, callus induction, shoot proliferation and wilting was recorded from day 2 to 14 every 24 hours.

TABLE 1

Growth promoting activity of methanone-(3',4'5'-trimethoxy) phenyl, 1-naphthyl, 2-O-4"-ethyl but-2"-enoate using Bacopa sensor system

| Test | Shoot Elongation (cms) | Branching (nos) | Root Elongation (cms) | Number of Leaves (nos) | Number of Roots (nos) | Browning Yellowing Death |
|---|---|---|---|---|---|---|
| Control | 1.0 | 2.0 | 0.8 | 5.0 | 2 + 2 | Nil |
| Compound 1 | 1.6 | 2.0 | 0.8 | 11.0 | 2 + 2 | Nil |

Example 2

Growth Promoting Activity of Compound 1 Using Aromatic Plant Species Mentha Arvensis To confirm the growth promoting activity of methanone-(3',4',5'-trimethoxy) phenyl, 1-naphthyl, 2-O-4"-ethyl but-2"-enoate, it was tested with a medicinal and aromatic plant species *Mentha arvensis*. The explants used were 0.5 cm long pieces of the second and third internodes of the shoots formed from axillary buds and culture. The internode segments were inoculated in MS basal media (Murashige and Skoog, 1962, *Physiol. Planta.* 15: pp. 473 to 497) containing vitamins 100 µg/ml, myo-inositol 3%, w/v, sucrose 1.5% w/v, Agar and different concentrations of auxins and cytokinin. Different concentrations of 1-naphthalene acetic acid (NM) (0.0, 0.2, 2.0 µg/ml) were used in combination with different concentrations of 6 benzyl amino purine (BAP) (0, 10 & 5 µg/ml). On each kind of media 10 replicates of the explants were inoculated into three petriplates with each plates containing 4 explants. Compound 1 was serially replaced with each concentration of NM and BAP individually to observe its growth promoting activity. The experiment was arranged in the form of a completely randomized design (CRD).

Cultures were maintained at 25±2° C. and 400 to 600 lux light intensity with 16 h photoperiod. The response of explants was recorded every 24 h over 4 week periods. Each explant was observed at 2 week intervals and sub cultured on same fresh medium. The proportional increase in biomass was recorded by taking the fresh weight of the growing tissue during sub culturing and dividing the increase with the initial weight.

At the end of 12 weeks from inoculation the shoots were separated and individually transferred to MS basal media containing vitamins for rooting. The rooted plantlets were subsequently transferred to pods in a green house.

Composition of Medium A2:

The basal medium for studying the response was MS 0 (Murashige and Skoog, 1962, *Physiol. Planta.* 15: pp. 473 to 497) supplemented with 0.2 mg/L IAA (indole acetic acid) and 5 mg/L BAP (benzene amino purine).

Composition of Medium A3:

The basal medium for studying the response was MS 0 (Murashige and Skoog, 1962, *Physiol. Planta.* 15: pp. 473 to 497) supplemented with 2mg/L IAA (indole acetic acid) and 10 mg/L BAP (benzene amino purine).

TABLE 2

Growth promoting activity of Methanone- (3',4',5'-trimethoxy) phenyl, 1-naphthyl, 2-O-4"-ethyl but-2"-enoate with *Mentha arvensis*

| Medium | Concentration of growth regulators in MS basal Medium | | | Number of shoots observed after three weeks |
|---|---|---|---|---|
| | IAA | BAP | Compound 1 | |
| A3 | 2.0 | 10.0 | — | 2–3 shoots per explant |
| | — | 10.0 | 2.0 | 3–4 shoots per explant (single root in one replication) |
| | 2.0 | — | 10.0 | No growth |
| A2 | 0.2 | 5.0 | — | 1–2 shoots per explant (No roots) |
| | — | 5.0 | 0.2 | 1–2 shoots per explant (No roots) |
| | 0.2 | — | 5.0 | Plant death |

Example 3

Synthesis of the Bioactive Compound Methanone-(3',4',5'-trimethoxy) phenyl, 1-naphthyl, 2-O-4"-ethyl but-2"-enoate (a) Methylating gallic acid by treating it with a methylating agent and an alkali compound in a suitable organic solvent reaction medium to 3,4,5-trimethoxy benzoic acid [Gallic acid is 3,4,5-trihydroxybenzoic acid, $C_6H_2(OH)_3CO_2H$, colorless, odorless, crystalline organic acid found in gallnuts, sumach, tea leaves, oak bark, and many other plants, both in its free state and as part of the tannin molecule (gallotannin) (Columbia Encyclopedia, Sixth Edition, Copyright 2003). There are reports on several derivatives of gallic acid having different pharmaceutical activities.];

(b) Reacting 3,4,5-trimethoxy benzoic acid with 2-naphthol in the presence of a carboxylic acid activator in the presence of a suitable base and an appropriate organic solvent medium and then condensing and purifying the product through suitable column chromatography;

(c) Subjecting the condensed product to Fries rearrangement in the presence of an appropriate Lewis acid at a temperature of 60 to 130° C., followed by purification by suitable column chromatography of the phenolic naphthophenone derivative; and (d) Treating the phenolic naphthophenone derivative with an alkyl halo crotonate in a suitable reaction medium consisting of a base and a suitable organic solvent to yield methanone-(3',4',5'-trimethoxy) phenyl, 1-naphthyl, 2-O-4"-ethyl but-2"-enoate.

The methylating agent used in step (a) is selected from dimethyl sulphate and methyl iodide.

The alkali compound used in step (a) is selected from sodium hydroxide, potassium hydroxide and lithium hydroxide.

The organic solvent used in step (a) is selected from water, methanol and acetone.

The carboxylic acid activator used in step (b) is selected from DCC and EDC.

The base used in used in step (b) with carboxylic acid activator is selected from DMAP and TEA.

The organic solvent used in step (b) is selected from dichloromethane and dimethyl formamide.

The column chromatography adsorbent used in step (b) is selected from silica gel, silicic acid and fluorosil.

The Lewis acid used in step (c) is selected from aluminum chloride, zinc chloride and polyphosphoric acid.

The column chromatography adsorbent used in step (c) is selected from silica gel, silicic acid and fluorosil.

The alkyl halo crotonate used in the step (d) to etherify the phenolic naphthophenone is selected from methyl chloro crotonate, methyl bromo crotonate and ethyl bromo crotonate.

The base used in the etherification reaction in step (d) is selected from potassium hydroxide, sodium hydroxide and potassium carbonate.

The organic solvent used in the step (d) is selected from dimethyl formamide, acetone and methanol.

The products of the reactions as described in the steps (a) to (d) above are represented hereunder by the following formulas.

Step (a):

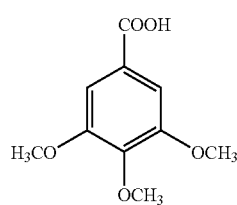

$C_{10}H_{12}O_5$ (3,4,5-trimethoxy benzoic acid-Formula 3)

Step (b):

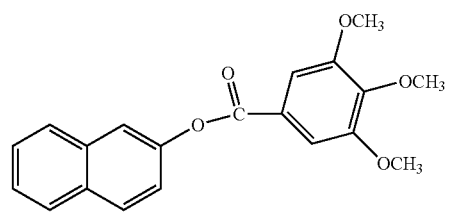

$C_{20}H_{18}O_5$ (2-O-naphthyl, 3', 4', 5'-trimethoxy benzoate-Formula 4)

Step (c):

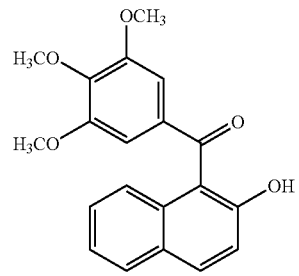

$C_{17}H_{18}O_5$ (methanone-(3',4',5'-trimethoxy) phenyl, 1-naphthyl, 2-ol-Formula 5)

Step (d):

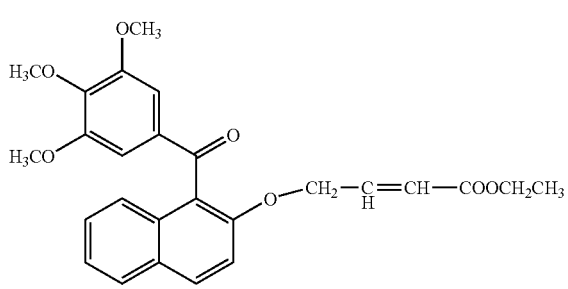

$C_{26}H_{26}O_7$ (methanone-(3',4',5'-trimethoxy) phenyl, 1-naphthyl, 2-O-4"-ethyl but-2"-enoate-Formula 1).

The invention claimed is:

1. A synthetic plant growth regulator compound, methanone-(3',4',5'-trimethoxy) phenyl, 1-naphthyl, 2-O4"-ethyl but-2"-enoate having a structural as represented by Formula 1:

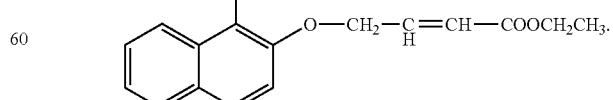

Formula 1

2. A compound, ethanone-(3',4',5'-trimethoxy) phenyl, 1-naphthyl, 2-ol, having a structural as represented by Formula 5, capable of plant growth regulation:

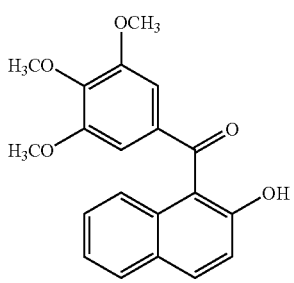

Formula 5

3. A method for regulating plant growth comprising applying to a plant a synthetic plant growth regulator compound, methanone-(3',4',5'-trimethoxy) phenyl, 1-naphthyl, 2-O-4"-ethyl but-2"-enoate having a structural as represented by Formula 1:

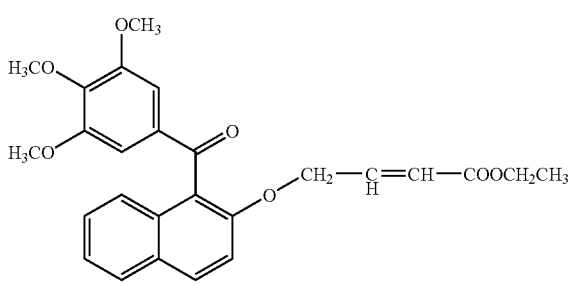

Formula 1 wherein the compound has auxin like plant growth regulatory activity.

4. The method of claim 3, which method provides enhancement of shoot elongation by about 2 cm within 15 days.

5. The method of claim 4, which method provides enhancement of the shoot elongation by about 1.6 cm within 15 days.

6. The method of claim 3, which method provides production of about 2 to 5 shoots within three weeks in medium A3.

7. The method of claim 6, which method provides production of about 3 to 4 shoots within three weeks in medium A3.

8. The method of claim 3, which method enhances callus formation and shoot differentiation.

9. A process for preparing a compound having a structure according to Formula 1 (methanone-(3',4',5'-trimethoxy) phenyl, 1-naphthyl, 2-O-4"-ethyl but-2"-enoate), the process comprising the steps of:

(a) methylating gallic acid by treating it with a methylating agent and an alkali compound in a suitable solvent reaction medium to obtain an intermediate having a structure represented by Formula 3 (3,4,5-trimethoxy benzoic acid):

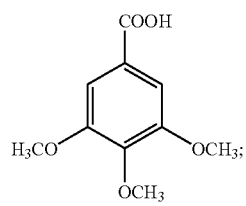

Formula 3

(b) reacting the 3,4,5-trimethoxy benzoic acid obtained in step (a) with 2-naphthol in the presence of a carboxylic acid activator in the presence of a suitable base and an organic solvent to obtain an intermediate compound having a structure as represented by Formula 4

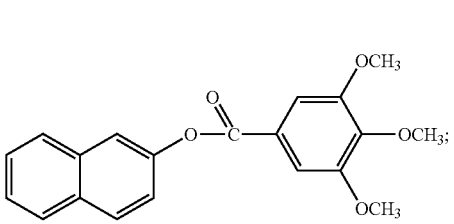

Formula 4

(c) purifying the compound having the structure as represented by Formula 4, obtained in the step (b), by column chromatography;

(d) subjecting the compound having the structure as represented by

Formula 4, obtained in step (c), to Fries rearrangement in presence of appropriate Lewis acid at a temperature in the range of about 50 to about 150° C., followed by purification by column chromatography to yield an intermediate having a structure represented by Formula 5;

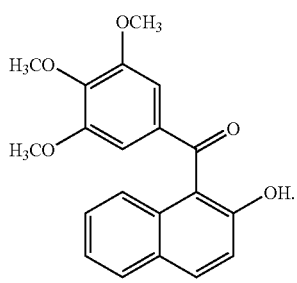

Formula 5 and a yield in the range of about 15 to about 40%; and (e) reacting the intermediate having structural Formula 5 from step (d) with an alkyl halo-crotonate in a suitable reaction medium consisting of a base and a suitable organic solvent to yield methanone-(3',4',5'-trimethoxy) phenyl, 1-naphthyl, 2-O-4"-enoate, having a structure represented by Formula 1, with a yield in the range of about 45 to about 75%.

10. The process of claim 9, wherein methylating agent in step (a) is selected from the group comprising dimethyl sulphate or methyl iodide.

11. The process of claim 10, wherein the methylating agent used in step (a) is dimethyl sulphate.

12. The process of claim 9, wherein the amount of methylating agent used in step (a) is in the range of about 20 to about 30 ml/l.

13. The process of claim 12, wherein the amount of methylating agent used in step (a) is in the range of about 21 to about 28 ml/l.

14. The process of claim 9, wherein the alkali compound used in step (a) is selected from sodium hydroxide, potassium hydroxide or lithium hydroxide.

15. The process of claim 14, wherein the alkali compound used is sodium hydroxide or potassium hydroxide.

16. The process of claim 9, wherein the amount of alkali compound used in step (a) is in the range of about 10 to about 25 g/l.

17. The process of claim 16, wherein the amount of alkali compound used in step (a) is in the range of about 16 to about 20 g/l.

18. The process of claim 9, wherein the solvent used in step (a) is selected from water, methanol and acetone.

19. The process of claim 18, wherein the solvent used in the step (a) is water.

20. The process of claim 9, wherein the amount of solvent used in step (a) is in the range of about 50 about 120 ml/l.

21. The process of claim 20, wherein the amount of solvent used in step (a) is in the range of about 60 to about 100 ml/l.

22. The process of claim 9, wherein the amount of 2-naphthol used in step (b) is in the range of about 2 to about 5 g/l.

23. The process of claim 22, wherein the amount of 2-naphthol used in step (b) is in the range of about 3.6 to about 4 g/l.

24. The process of claim 9, wherein the activator used in step (b) is selected from dicyclohexyl carbodiimide (DCC) and N-(3-dimethylaminopropyl)-N'-ethyl carbodiimide hydrochloride (EDC).

25. The process of claim 24, wherein activator used in step (b) is DCC.

26. The process of claim 9, wherein the amount of activator used in step (b) is in the range of about 2 to about 5 g/l.

27. The process of claim 26, wherein the amount of activator used in step (b) is in the range of about 3.6 to about 4 g/l.

28. The process of claim 9, wherein the base used in step (b) is selected from dimethyl amino pyridine (DMAP) and triethyl amine (TEA).

29. The process of claim 9, wherein the amount of base used in step (b) is in the range of about 25 to about 60 g/l.

30. The process of claim 29, wherein the amount of base used in step (b) is in the range of about 30 to about 50 g/l.

31. The process of claim 9, wherein the organic solvent used in step (b) is selected from dichloromethane or dimethyl formamide.

32. The process of claim 31, wherein the organic solvent used in step (b) is dichloromethane.

33. The process of claim 9, wherein the amount of organic solvent used in step (b) is in the range of about 30 to about 80 ml/l.

34. The process of claim 33, wherein the amount of organic solvent used in step (b) is in the range of about 40 to about 70 ml/l.

35. The process of claim 9, wherein in the column chromatography of steps (c) and (d) the adsorbent is selected from silica gel, silicic acid or fluorosil.

36. The process of claim 35, wherein the adsorbent used is silica gel.

37. The process of claim 9, wherein the temperature in step (d) is in the range of about 60 to about 130° C.

38. The process of claim 9, wherein the Lewis acid used in step (d) is selected from aluminum chloride, zinc chloride or polyphosphoric acid.

39. The process of claim 38, wherein the Lewis acid used in step (d) is aluminum chloride.

40. The process of claim 9, wherein the amount of Lewis acid used in step (d) is in the range of about 1 to about 5 g/l.

41. The process of claim 40, wherein the amount of Lewis acid used in step (d) is in the range of about 2 to about 3 g/l.

42. The process of claim 9, wherein the yield of methanone-(3',4',5'-trimethoxy) phenyl, 1-naphthyl, 2-ol intermediate, having a structure represented by Formula 5 in step (d) is in the range of about 20 to about 31.2%.

43. The process of claim 9, wherein the alkyl halo crotonate used in step (e) is selected from methyl chloro crotonate, methyl bromo crotonate or ethyl bromo crotonate.

44. The process of claim 43, wherein the alkyl halo crotonate used in step (e) is ethyl bromo crotonate.

45. The process of claim 9, wherein the amount of alkyl halo crotonate used in step (e) is in the range of about 0.1 to about 1.5 ml/l.

46. The process of claim 45, wherein the amount of alkyl halo crotonate used in step (e) is in the range of about 0.2 to about 0.5 ml/l.

47. The process of claim 9, wherein the base used in step (e) is selected from potassium hydroxide, sodium hydroxide or potassium carbonate.

48. The process of claim 47, wherein the base used in step (e) is potassium carbonate.

49. The process of claim 9, wherein the amount of base used in step (e) is in the range of about 0.5 to about 3 g/l.

50. The process of claim 49, wherein the amount of base used in step (e) is in the range of about 1 to about 2 g/l.

51. The process of claim 9, wherein the organic solvent used in step (e) is selected dimethyl formamide, acetone or methanol.

52. The process of claim 51, wherein the organic solvent used in step (e) is acetone.

53. The process of claim 9, wherein the amount of organic solvent used in step (e) is in the range of about 5 to about 15 ml/l.

54. The process of claim 53, wherein the amount of organic solvent used in step (e) is in the range of about 6 to about 10 ml/l.

55. The process of claim 9, wherein the yield of methanone-(3',4',5'-trimethoxy) phenyl, 1-naphthyl, 2-O-4"-ethyl but-2"-enoate, having a structure represented by Formula 1 in step (e) is in the range of about 47 to about 70%.

* * * * *

UNITED STATES PATENT AND TRADEMARK OFFICE
CERTIFICATE OF CORRECTION

PATENT NO. : 7,135,590 B2  Page 1 of 1
APPLICATION NO. : 10/919567
DATED : November 14, 2006
INVENTOR(S) : Khanuja et al.

It is certified that error appears in the above-identified patent and that said Letters Patent is hereby corrected as shown below:

On Title Page
Inventors (Item 75), replace "Sunia Kumar Chattopadhyay" with --Sunil Kumar Chattopadhyay--.
Inventors (Item 75), replace "Kachin Srivastava" with --Sachin Srivastava--.

Signed and Sealed this

Twentieth Day of February, 2007

JON W. DUDAS
*Director of the United States Patent and Trademark Office*